United States Patent
Ishibahsi et al.

(10) Patent No.: US 7,569,699 B2
(45) Date of Patent: Aug. 4, 2009

(54) PROCESS FOR PRODUCING EPOXYTRIAZOLE DERIVATIVE

(75) Inventors: Taro Ishibahsi, Nagaokakyo (JP); Hideo Muraoka, Toyonaka (JP); Tadashi Mizuno, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 74 days.

(21) Appl. No.: 11/791,511

(22) PCT Filed: Nov. 29, 2005

(86) PCT No.: PCT/JP2005/022258

§ 371 (c)(1),
(2), (4) Date: May 24, 2007

(87) PCT Pub. No.: WO2006/059759

PCT Pub. Date: Jun. 8, 2006

(65) Prior Publication Data

US 2008/0081915 A1    Apr. 3, 2008

(30) Foreign Application Priority Data

Nov. 30, 2004  (JP) .............................. 2004-345719

(51) Int. Cl.
*C07D 249/02* (2006.01)
(52) U.S. Cl. ................. 548/262.4; 548/262.2; 549/547; 549/552
(58) Field of Classification Search ............. 548/262.2, 548/262.4; 549/552, 547
See application file for complete search history.

(56) References Cited

U.S. PATENT DOCUMENTS

| | | | |
|---|---|---|---|
| 4,668,660 A | 5/1987 | Paessens et al. | |
| 5,366,989 A | 11/1994 | Imaizumi et al. | |
| 5,981,560 A | 11/1999 | Bell et al. | |
| 6,884,892 B2 | 4/2005 | Wang et al. | |
| 2003/0236419 A1* | 12/2003 | Wang et al. | 548/267.8 |

FOREIGN PATENT DOCUMENTS

CA  1329995  11/1988

WO  WO 2004/018485 A1  3/2004

OTHER PUBLICATIONS

Saji et al., Bull. Chem. Soc. Jpn, 67, 1427-1433, 1994.*
Juodvirsis, Arvydas et al., "Synthesis and Properties of Pure 1,2,4-Triazole Sodium Salt and Its Use for Preparation of Fungicides", Chemija, vol. 10, No. 1, 1999, pp. 48-50, XP009106275.
Kazhemekaite, M. et al., "Preparation of the Pure Sodium Salt of 1H-1,2,4-Triazole"; Chemistry of Heterocyclic Compounds, vol. 34, No. 2, 1998, pp. 252-253, XP002497464.

* cited by examiner

*Primary Examiner*—Janet L Andres
*Assistant Examiner*—David E Gallis
(74) *Attorney, Agent, or Firm*—Foley & Lardner LLP

(57) ABSTRACT

This invention provides a process for producing an epoxytriazole derivative represented by formula (2):

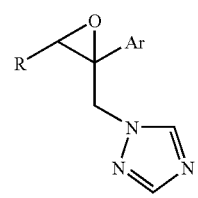

(2)

(wherein R and Ar are defined below),
which comprises a step including a reaction of an epoxy derivative represented by formula (1'):

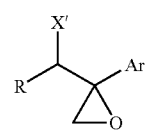

(1')

(wherein R represents a hydrogen atom or C1-12 alkyl group and Ar represents an aromatic group optionally substituted by a halogen atom(s) or trifluoromethyl group(s), and X' represents a hydroxy group or leaving group), with 1,2,4-triazole in the presence of a base and water.

25 Claims, No Drawings

US 7,569,699 B2

PROCESS FOR PRODUCING EPOXYTRIAZOLE DERIVATIVE

TECHNICAL FIELD

This invention directs to a synthetic intermediate for a triazole compound which is useful as an antifungal agent, especially an epoxytriazole derivative, and a process for producing its intermediate.

BACKGROUND ARTS

An epoxytriazole derivative represented by formula (2):

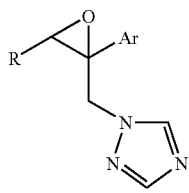

(wherein R represents a hydrogen atom or C1-12 alkyl group and Ar represents an aromatic group optionally substituted by a halogen atom(s) or a trifluoromethyl group(s)), is a synthetic intermediate for a triazole compound which is useful as an antifungal agent (e.g., JP-H05-230038A, JP-H04-356471A). It is known that the epoxytriazole derivative is prepared by a process comprising a step of making an epoxy compound represented by formula (1z):

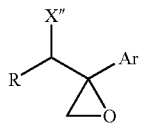

(wherein X″ represents an optionally protected hydroxy group or leaving group, and R and Ar are defined above), react with 1,2,4-triazole in the presence of a base.

For example, proposed are a process of the reaction using a water-prohibitive base such as sodium hydride and potassium tert-butoxide (e.g., JP-H04-74168A, WO2004/000826A, JP-2001-48873A, WO99/29675A, Chemical & Pharmaceutical Bulletin, 1992, Vol.40, No.2, p. 562-564), a process of the reaction in an aprotic solvent such as dimethyl sulfoxide and N,N-dimethylformamide dissolving potassium carbonate, potassium hydroxide or the like (e.g., WO2004/018486A, JP-H05-213906A, Heterocycles, 1998, Vol.49, p. 181-190) and a process of the reaction using a solid metal salt of 1,2,4-triazole prepared from a base and 1,2,4-triazole.

In the process using a water-prohibitive base, anhydrous solvent is required for the reaction and the process should be strictly controlled of moisture since the base is water-prohibitive. Further, even in the process of the reaction in the aprotic solvent dissolving potassium carbonate, potassium hydroxide or the like, an anhydrous base and anhydrous solvent are required. Furthermore, in the process of the reaction using a solid metal salt of 1,2,4-triazole, it is required that the metal salt of 1,2,4-triazole should be prepared from a base and 1,2,4-triazole and isolated in advance, and the steps including filtration and transport of powders or slurry are troublesome.

DISCLOSURE OF THE INVENTION

One object of the present invention is to provide a process of producing the epoxytriazole derivative (2), which is advantageous in industry and which is required of neither the use of water-prohibitive materials or anhydrous materials or the troublesome procedures of preparation and isolation of the metal salt of 1,2,4-triazole.

The present inventors have earnestly studied for solving these problems, and completed the present invention.

Namely, the invention includes the followings:

<1> A process for producing an epoxytriazole derivative represented by formula (2):

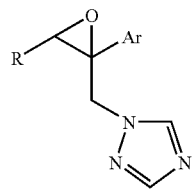

(wherein R and Ar are defined below), (hereinafter, referred to as the epoxytriazole derivative (2) as the case may be) which comprises a step including a reaction of an epoxy derivative represented by formula (1'):

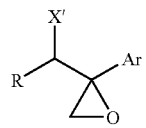

(wherein R represents a hydrogen atom or C1-12 alkyl group and Ar represents an aromatic group optionally substituted by a halogen atom(s) or trifluoromethyl group(s), and X' represents a hydroxy group or leaving group), (hereinafter, referred to as the epoxy derivative (1') as the case may be) with 1,2,4-triazole in the presence of a base and water.

<2> The process described in <1>, wherein the epoxy derivative (1') is an epoxy compound represented by formula (1):

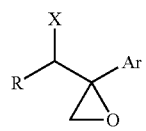

(wherein X represents a leaving group, and R and Ar are defined above), (hereinafter, referred to as the epoxy compound (1) as the case may be).

<3> The process described in <2>, wherein the leaving group is $-SO_2R^2$ (wherein $R^2$ represents an optionally substituted C1-12 alkyl group or optionally substituted aromatic group).

<4> The process described in <3>, wherein R² is a methyl group.

<5> The process described in any one of <2> to <4>, wherein Ar is a difluorophenyl group.

<6> The process described in <5>, wherein the difluorophenyl group is a 2,4-difluorophenyl group or 2,5-difluorophenyl group.

<7> The process described in any one of <2> to <6>, wherein R is a methyl group.

<8> The process described in any one of <2> to <7>, wherein the base is at least one selected from the group consisting of alkali metal hydroxide, alkaline earth metal hydroxide, alkali metal carbonate and alkaline earth metal carbonate.

<9> The process described in <8>, wherein the alkali metal is sodium or potassium and the alkaline earth metal is calcium or magnesium in at least one selected from the group consisting of alkali metal hydroxide, alkaline earth metal hydroxide, alkali metal carbonate and alkaline earth metal carbonate.

<10> The process described in <3>, wherein the epoxy compound (1), wherein X is a —SO₂R² (wherein R² is defined above), is obtained by the reaction of an epoxy compound represented by formula (1″):

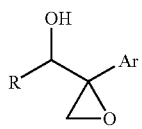

(1″)

(wherein R and Ar are defined above), (hereinafter, referred to as the epoxy compound (1″) as the case may be) with a sulfonyl halide represented by formula (6):

Y'SO₂R²

(wherein Y' represents a chlorine atom or bromine atom and R² is defined above), (hereinafter, referred to as the sulfonyl halide (6) as the case may be) or a sulfonic anhydride represented by formula (7):

O(SO₂R²)₂

(wherein R² is defined above), (hereinafter, referred to as the sulfonic anhydride as the case may be).

<11> The process described in <1>, wherein the epoxy derivative (1') is the epoxy derivative (1″), the step provides a dihydroxy compound represented by formula (3):

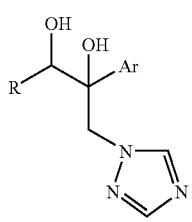

(3)

(wherein R and Ar are defined above), (hereinafter, referred to as the dihydroxy compound (3) as the case may be) and further the process comprises a step of a reaction of the dihydroxy compound (3) with a compound represented by formula (5):

R¹SO₂Y (5)

(wherein R¹ represents an optionally substituted C1-12 alkyl group or optionally substituted aromatic group and Y represents a chlorine atom or bromine atom), (hereinafter, referred to as the compound (5) as the case may be) in the presence of a base.

<12> The process described in <11>, wherein the epoxytriazole derivative (2) is an optically active isomer.

<13> The process described in <11> or <12>, wherein Ar is a difluorophenyl group.

<14> The process described in <13>, wherein the difluorophenyl group is a 2,4-difluorophenyl group or 2,5-difluorophenyl group.

<15> The process described in any one of <11> to <14>, wherein R is a methyl group.

<16> The process described in any one of <11> to <16>, wherein the base for the reaction step with 1,2,4-triazole is at least one selected from the group consisting of alkali metal hydroxide, alkaline earth metal hydroxide, alkali metal carbonate and alkaline earth metal carbonate.

<17> The process described in <16>, wherein the alkali metal is sodium or potassium and the alkaline earth metal is calcium or magnesium in alkali metal hydroxide, alkaline earth metal hydroxide, alkali metal carbonate and alkaline earth metal carbonate.

<18> The process described in any one of <11> to <17>, wherein the base for the reaction step of the dihydroxy compound represented by formula (3) with the compound represented by formula (5) is at least one selected from the group consisting of organic amine, alkali metal hydroxide and alkali metal carbonate.

<19> The process described in <18>, wherein the organic amine is triethylamine or pyridine and the alkali metal for the alkali metal hydroxide and alkali metal carbonate is sodium or potassium.

<20> The process for producing the dihydroxy compound (3) which comprises making the epoxy compound (1″) react with 1,2,4-triazole in the presence of a base and water.

<21> The process described in <20>, wherein Ar is a difluorophenyl group.

<22> The process described in <21>, wherein the difluorophenyl group is 2,4-difluorophenyl group or 2,5-difluorophenyl group.

<23> The process described in any one of <20> to <22>, wherein R is a methyl group.

<24> The process described in any one of <20> to <23>, wherein the base is at least one selected from the group consisting of alkali metal hydroxide, alkaline earth metal hydroxide, alkali metal carbonate and alkaline earth metal carbonate.

<25> The process described in <24>, wherein the alkali metal is sodium or potassium and the alkaline earth metal is calcium or magnesium in alkali metal hydroxide, alkaline earth metal hydroxide, alkali metal carbonate and alkaline earth metal carbonate.

BEST MODE FOR CARRYING OUT THE INVENTION

The present invention is explained in detail below.

By making the epoxy derivative (1') react with 1,2,4-triazole in the presence of a base and water, the epoxytriazole derivative (2) is obtained in case that X' is a leaving group, namely that the epoxy derivative (1') is the epoxy compound (1), and the dihydroxy compound (3) is obtained in case that X' is a hydroxy group, namely the epoxy derivative (1') is the epoxy compound (1"). Further, the epoxytriazole derivative (2) can be obtained by making this dihydroxy compound (3) react with the compound (5) in the presence of a base.

In the present invention, the epoxy derivative (1') can be prepared according to the methods described in JP-H05-154377A, WO2004/000826A and the like. For example, the epoxy compound (1"), wherein X' is a hydroxy group, can be obtained by making a lactate ester derivative or lactamide derivative lead to an aromatic ketone compound represented by formula (4):

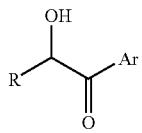

(4)

(wherein R and Ar are defined above), through the reaction with an aromatic Grignard reagent, and then, subjecting the aromatic ketone compound to epoxidation by a trimethylsulfoxonium halide.

Further, the epoxy compound (1), wherein X' is a leaving group, can be obtained by converting the hydroxy group of the above-mentioned epoxy compound (1") to a leaving group X.

R is a hydrogen atom or C1-12 alkyl group, and examples of the alkyl group include methyl group, ethyl group, n-propyl group, iso-propyl group, n-butyl group, sec-butyl group, tert-butyl group, pentyl group, iso-pentyl group, neopentyl group, n-hexyl group, cyclohexyl group, heptyl group, octyl group, nonyl group, decyl group, undecyl group and dodecyl group. Preferable are methyl group, ethyl group, n-propyl group, iso-propyl group and tert-butyl group, and more preferable is methyl group.

Ar is an aromatic group, an aromatic group substituted by a halogen atom(s) or an aromatic group substituted by a trifluoromethyl group(s), and examples of the halogen atom include fluorine atom, chlorine atom, bromine atom and iodine atom. Fluorine atom is preferable.

Typical examples of Ar include phenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-iodophenyl group, 3-iodophenyl group, 4-iodophenyl group, 2,3-difluorophenyl group, 2,4-difluorophenyl group, 2,5-difluorophenyl group, 3,4-difluorophenyl group, 3,5-difluorophenyl group, 2,6-difluorophenyl group, 2,3-dichlorophenyl group, 2,4-dichlorophenyl group, 2,5-dichlorophenyl group, 3,4-dichlorophenyl group, 3,5-dichlorophenyl group, 2,6-dichlorophenyl group, 2,3-dibromophenyl group, 2,4-dibromophenyl group, 2,5-dibromophenyl group, 3,4-dibromophenyl group, 3,5-dibromophenyl group, 2,6-dibromophenyl group, 2,4,6-trifluorophenyl group, 2-(trifluoromethyl)phenyl group, 3-(trifluoromethyl)phenyl group and 4-(trifluoromethyl)phenyl group. Preferable are 2,4-difluorophenyl group, 2,5-difluorophenyl group, 2,4,6-trifluorophenyl group, 2-(trifluoromethyl)phenyl group, 3-(trifluoromethyl)phenyl group and 4-(trifluoromethyl)phenyl group. More preferable are 2,4-difluorophenyl group and 2,5-difluorophenyl group.

Examples of the leaving group of X and X' include halogen atoms and a group represented by formula (8):

(8)

(wherein $R^2$ represents an optionally substituted C1-12 alkyl group or an optionally substituted aromatic group).

Typical examples of the halogen atom include chlorine atom and bromine atom. Typical examples of the C1-12 alkyl group of $R^2$ include methyl group, ethyl group, n-propyl group, iso-propyl group, n-butyl group, sec-butyl group, tert-butyl group, pentyl group, iso-pentyl group, neopentyl group, n-hexyl group, cyclohexyl group, heptyl group, octyl group, nonyl group, decyl group, undecyl group and dodecyl group. Preferable are methyl group, ethyl group, n-propyl group, iso-propyl group and tert-butyl group, and more preferable is methyl group. Examples of the aromatic group of $R^2$ include the same examples as Ar mentioned above.

Examples of the substituted alkyl group include phenyl-substituted alkyl groups such as benzyl group, 2-phenylethyl group and 1-phenylethyl group; and fluoroalkyl groups such as trifluoromethyl group and pentafluoroethyl group. Examples of the substituted aryl group include methylphenyl group and ethylphenyl group.

Examples of the group represented by formula (8) include methylbenzenesulfonyloxy group, benzenesulfonyloxy group, methanesulfonyloxy group, benzylsulfonyloxy group and trifluoromethanesulfonyloxy group. Preferable are 4-methylbenzenesulfonyloxy group and methanesulfonyloxy group, and more preferable is methanesulfonyloxy group.

Examples of $R^1$ of the compound (5) include the same examples as $R^2$ mentioned above.

The epoxy derivative (1'), epoxy compound (1) and epoxy compound (1") include all optically active compounds and mixtures thereof (e.g., racemate, enantiomer mixture, diastereomer mixture) which can exist.

The epoxytriazole derivative (2) has a 1,2,4-triazole ring and it may be a salt form. Examples include additives with mineral acids such as hydrochloric acid, sulfuric acid, nitric acid and phosphoric acid and organic acids such as acetic acid and methanesulfonic acid.

Process for Producing the Epoxytriazole Derivative (2) from the Epoxy Compound (1) (Hereinafter, Referred to as Process A as the Case May be)

The epoxytriazole derivative (2) can be produced by making the epoxy compound (1) react with 1,2,4-triazole in the presence of a base and water.

The base used for the reaction is not restricted so long as it can be dissolved in water, the solvent or reaction solvent described below, and alkali metal hydroxide, alkaline earth metal hydroxide, alkali metal carbonate and alkaline earth metal carbonate are preferable. Typical examples of the alkali metal hydroxide include sodium hydroxide, potassium hydroxide, lithium hydroxide and cesium hydroxide, and typical examples of the alkaline earth metal hydroxide include calcium hydroxide and magnesium hydroxide. Typical examples of the alkali metal carbonate include sodium carbonate and potassium carbonate, and typical examples of the alkaline earth metal carbonate include calcium carbonate and magnesium carbonate. Preferable are sodium hydroxide, potassium hydroxide, calcium hydroxide, sodium carbonate and potassium carbonate. More preferable are sodium hydroxide and potassium hydroxide.

The amount of the base is usually 0.3 to 1.3 mols, preferably 0.5 to 1.1 mols, more preferably 0.8 to 1 mol per 1 mol of 1,2,4-triazole with a view to preventing the remains of 1,2,4-triazole and avoiding a reduction in the yield or quality by side reaction.

The amount of 1,2,4-triazole is usually 0.8 to 5 mols, preferably 1 to 3 mols, more preferably 1.1 to 2 mols per 1 mol of the epoxy compound (1) in view of the yield and economy.

The amount of water is usually 5 to 50 mols, preferably 10 to 30 mols per 1 mol of the epoxy compound (1).

Any solvent can be used so long as it does not inhibit the reaction. Water may also be used as a solvent. In particular, a mixed solvent of water and an organic solvent is preferably used in practice. When the mixed solvent of water and an organic solvent, the reaction system can be homogeneous or the phases can be separated in the reaction.

Examples of the solvent include ether solvents such as tetrahydrofuran (THF), methyl tert-butyl ether, 1,4-dioxane, diethylene glycol dimethyl ether (diglyme), ethylene glycol dimethyl ether, 1,3-dioxolane and 2-methyltetrahydrofuran; aprotic solvents such as N,N-dimethylformamide (DMF), N,N-dimethylacetamide (DMAc), dimethyl sulfoxide (DMSO), sulfolane, N-methyl-2-pyrrolidinone (NMP), 1,3-dimethyl-2-imidazolidinone (DMI), hexamethylphosphoramide (HMPA), nitrobenzene, carbon disulfide, acetonitrile and propionitrile; halogenated hydrocarbon solvents such as methylene chloride, 1,2-dichloroethane, chlorobenzene and 2-chlorotoluene; hydrocarbon solvents such as hexane, cyclohexane, heptane, toluene and xylene; alcohol solvents such as methanol, ethanol, n-propanol, iso-propanol, n-butanol, iso-butanol, tert-butanol, ethylene glycol and diethylene glycol; and ketone solvents such as acetone, methyl ethyl ketone (MEK), methyl isobutyl ketone (MIBK) and cyclohexanone. Among them, preferable are THF, DMF, DMSO, toluene, methanol, ethanol, iso-propanol and acetone, and more preferable are DMF, DMSO and iso-propanol.

The amount of the solvent is usually 0.5 L to 30 L, preferably 0.8 L to 25 L, more preferably 1 L to 20 L per 1 kg of the epoxy compound (1).

Further, so-called phase transfer catalysts such as tetraalkylammonium salts (e.g., octadecyltrimethylammonium bromide, tetrabutylammonium sulfate, tetrabutylammonium bromide, tetrabutylammonium iodide, tetrabutylammonium chloride), and trialkylbenzylammonium salts (e.g., benzyltrimethylammonium bromide, benzyltrimethylammonium chloride, benzyltriethylammonium chloride) may be added for accelerating the reaction.

The order of adding or dropping of each reagent of the epoxy compound (1), base, 1,2,4-triazole, water and solvent is not restricted. For example, a method of dropping a mixture of the base, 1,2,4-triazole and water to a solution of the epoxy compound (1) and solvent, or a method of dropping an aqueous base solution to a mixture of the epoxy compound (1), 1,2,4-triazole and solvent is performed.

The reaction temperature depends on a kind of the solvent used for the reaction, and it is usually −20 to +150° C., preferably 0 to 100° C., more preferably 20 to 90° C.

The reaction time depends on the reaction temperature and the concentration of the epoxy compound (1), and it is usually 0.5 to 24 hours, preferably 1 to 15 hours, more preferably 3 to 10 hours.

The produced epoxytriazole derivative (2) can be isolated and purified by adopting conventional work-up and purification procedures such as extraction, phase separation, washing, concentration, crystallization, column chromatography and recrystallization. The epoxytriazole derivative (2) can also be provided without the purification for the reaction deriving to the objective medicament.

Process for Producing the Dihydroxy Compound (3) from the Epoxy Compound (1″) (Hereinafter, Referred to as Process B as the Case May be)

The dihydroxy compound (3) can be produced by the reaction of the epoxy compound (1″) with 1,2,4-triazole in the presence of a base and water.

The base used for the reaction is not restricted so long as it can be dissolved in the solvent or reaction solvent described below, and alkali metal hydroxide, alkaline earth metal hydroxide, alkali metal carbonate and alkaline earth metal carbonate are preferable. Typical examples of the alkali metal hydroxide include sodium hydroxide, potassium hydroxide, lithium hydroxide and cesium hydroxide, and typical examples of the alkaline earth metal hydroxide include calcium hydroxide and magnesium hydroxide. Typical examples of the alkali metal carbonate include sodium carbonate and potassium carbonate, and typical examples of the alkaline earth metal carbonate include calcium carbonate and magnesium carbonate. Preferable are sodium hydroxide, potassium hydroxide, calcium hydroxide, sodium carbonate and potassium carbonate. More preferable are sodium hydroxide and potassium hydroxide.

The amount of the base is usually 0.01 to 1 mol, preferably 0.05 to 0.8 mol, more preferably 0.1 to 0.5 mol per 1 mol of 1,2,4-triazole in view of the reaction rate, preventing the remains of 1,2,4-triazole, and avoiding a reduction in the yield or quality by side reaction.

The amount of 1,2,4-triazole is usually 0.8 to 5 mols, preferably 1 to 3 mols, more preferably 1.1 to 2 mols per 1 mol of the epoxy compound (1″) in view of the yield and economy.

The amount of water is usually 1 to 30 mols, preferably 2 to 20 mols per 1 mol of the epoxy compound (1″).

Any solvent can be used so long as it does not inhibit the reaction. Water may also be used as a solvent. In particular, a mixed solvent of water and an organic solvent is preferably used in practice. When the mixed solvent of water and an organic solvent is used, the reaction system can be homogeneous or the phases can be separated in the reaction.

Examples of the solvent include ether solvents such as tetrahydrofuran (THF), methyl tert-butyl ether, 1,4-dioxane, diethylene glycol dimethyl ether (diglyme), ethylene glycol dimethyl ether, 1,3-dioxolane and 2-methyltetrahydrofuran; aprotic solvents such as N,N-dimethylformamide (DMF), N,N-dimethylacetamide (DMAc), dimethyl sulfoxide (DMSO), sulfolane, N-methyl-2-pyrrolidinone (NMP), 1,3-dimethyl-2-imidazolidinone (DMI), hexamethylphosphoramide (HMPA), nitrobenzene, carbon disulfide, acetonitrile and propionitrile; halogenated hydrocarbon solvents such as methylene chloride, 1,2-dichloroethane, chlorobenzene and 2-chlorotoluene; hydrocarbon solvents such as hexane, cyclohexane, heptane, toluene and xylene; alcohol solvents such as methanol, ethanol, n-propanol, iso-propanol, n-butanol, iso-butanol, tert-butanol, ethylene glycol and diethylene glycol; and ketone solvents such as acetone, methyl ethyl ketone (MEK), methyl isobutyl ketone (MIBK) and cyclohexanone. Among them, preferable are THF, DMF, DMSO, toluene, methanol, ethanol, iso-propanol and acetone, and more preferable are DMF, DMSO and iso-propanol.

The amount of the solvent is usually 0.5 L to 30 L, preferably 0.8 L to 25 L, more preferably 1 L to 20 L per 1 kg of the epoxy compound (1″).

The order of adding or dropping of each reagent of the epoxy compound (1″), base, 1,2,4-triazole, water and solvent is not restricted. For example, a method of dropping a mixture of the base, 1,2,4-triazole and water to a solution of the epoxy compound (1") and solvent, or a method of dropping an aqueous base solution to a mixture of the epoxy compound (1"), 1,2,4-triazole and solvent is performed.

The reaction temperature depends on a kind of the solvent used for the reaction, and it is usually −20 to +150° C., preferably 0 to 100° C., more preferably 20 to 90° C.

The reaction time depends on the reaction temperature and the concentration of the epoxy compound (1"), and it is usually 0.5 to 24 hours, preferably 1 to 15 hours, more preferably 3 to 10 hours.

The produced dihydroxy compound (3) can be subjected to a conventional work-up procedure, for example, pouring the reaction liquid into water, phase separation, and then washing, drying and concentrating the organic layer, and the product can be provided for the following Process C as it is. The product can be optionally purified by silica gel column chromatography or recrystallization Process for Producing the Epoxytriazole Derivative (2) from the Dihydroxy Compound (3) (Hereinafter, Referred to as Process C as the Case May be)

The epoxytriazole derivative (2) can be produced by making the dihydroxy compound (3) react with the compound (5) in the presence of a base.

The amount of the compound (5) is usually 0.8 to 3 mols, preferably 1 to 2 mols, more preferably 1 to 1.5 mols per 1 mol of the epoxy compound (1") in view of the yield and a reduction of the side reaction.

Examples of the base used for Process C include aliphatic tertially amines such as trimethylamine, triethylamine, tributylamine, diisopropylethylamine and N-methylmorpholine; aromatic amines such as pyridine, picoline, 2,6-lutidine, colidine, 4-(N,N-dimethylamino)pyridine, N,N-dimethylaniline and N,N-diethylaniline; alkali metal hydroxides such as sodium hydroxide and potassium hydroxide; alkali metal carbonates such as sodium carbonate and potassium carbonate; and basic ion-exchange resins such as Amberlite IRA-67 and Amberlite IRA-900. Hereinafter, the above-mentioned aliphatic tertially amines and aromatic amines may be referred to as organic amines as the case may be. Triethylamine, pyridine and sodium hydroxide are preferable, and especially, triethylamine and sodium hydroxide are more preferable. These bases may be used solely or as a mixture of two or more, or used by adding two or more intermittently.

The amount of the base for Process C is usually 2 to 8 mols, preferably 3 to 6 mols per 1 mol of the compound (5) in view of the reaction rate, preventing the remains of the dihydroxy compound (3), and a reduction of the side reaction.

Any solvent can be used so long as it does not inhibit the reaction. Examples of the solvent include halogenated hydrocarbon solvents such as methylene chloride, 1,2-dichloroethane, monochlorobenzene, 1,2-dichlorobenzene, 2-chlorotoluene, 3-chlorotoluene, 4-chlorotoluene 2-chloro-m-xylene, 2-chloro-p-xylene, 4-chloro-o-xylene, 2,3-dichlorotoluene, 2,4-dichlorotoluene, 2,5-dichlorotoluene, 2,6-dichlorotoluene, 3,4-dichlorotoluene and monofluorobenzene; hydrocarbon solvents such as nitrobenzene and toluene; nitrile solvents such as acetonitrile and propionitrile; ether solvents such as methyl tert-butyl ether, ethylene glycol dimethyl ether, diethylene glycol dimethyl ether, tetrahydrofuran, 2-methyltetrahydrofuran, 1,3-dioxolane and 1,4-dioxane; and sulfur solvents such as carbon disulfide. Toluene is preferable. The solvent may be a mixture containing two or more solvents mentioned above, wherein any mixing ratio is available.

The amount of the solvent is usually 0.5 L to 30 L, preferably 0.8 L to 25 L, more preferably 1 L to 20 L per 1 kg of the epoxy compound (1") which is a raw material.

The order of adding of the reagents is not restricted. For example, a method of adding the dihydroxy compound (3) and a base to a solvent, and then adding the compound (5) thereto, or a method of adding the compound (3) and the compound (5) to a solvent, and then adding a base thereto is performed.

The reaction temperature depends on the raw materials and their ratio used for the reaction, and it is usually −30 to +80° C., preferably −10 to +60° C., more preferably −5 to +35° C.

The reaction time depends on the amount of the raw materials, and it is usually 0.5 to 24 hours, preferably 1 to 10 hours.

The epoxytriazole derivative (2) produced by Process C can be subjected to conventional work-up and purification procedures, for example, extraction, phase separation, washing, concentration, crystallization, column chromatography and recrystallization. The epoxytriazole derivative (2) can also be provided without the purification for the reaction deriving to the objective medicament.

The obtained epoxytriazole derivatives (2) includes all optically active compounds and mixtures thereof (e.g., racemate, enantiomer mixture, diastereomer mixture) which can exist. Typical examples include (2R,3S)-2-(2,4-difluorophenyl)-3-methyl-2-[(1H-1,2,4-triazol-1-yl)methyl]oxirane, (2R,3S)-2-(2,5-difluorophenyl)-3-methyl-2-[(1H-1,2,4-triazol-1-yl)methyl]oxirane, (2S,3R)-2-(2,4-difluorophenyl)-3-methyl-2-[(1H-1,2,4-triazol-1-yl)methyl]oxirane, (2S,3R)-2-(2,5-difluorophenyl)-3-methyl-2-[(1H-1,2,4-triazol-1-yl) methyl]oxirane, (2S,3S)-2-(2,4-difluorophenyl)-3-methyl-2-[(1H-1,2,4-triazol-1-yl)methyl]oxirane, (2S,3S)-2-(2,5-difluorophenyl)-3-methyl-2-[(1H-1,2,4-triazol-1-yl)methyl] oxirane, (2R,3R)-2-(2,4-difluorophenyl)-3-methyl-2-[(1H-1,2,4-triazol-1-yl)methyl]oxirane and (2R,3R)-2-(2,5-difluorophenyl)-3-methyl-2-[(1H-1,2,4-triazol-1-yl)methyl] oxirane. Preferable are (2R,3S)-2-(2,4-difluorophenyl)-3-methyl-2-[(1H-1,2,4-triazol-1-yl)methyl]oxirane and (2R,3S)-2-(2,5-difluorophenyl)-3-methyl-2-[(1H-1,2,4-triazol-1-yl)methyl]oxirane. These can be produced by adopting any method of deriving chemically from the optical isomer of the epoxy compound (1'); manufacturing by using the optical isomer mixtures (e.g., racemate, enantiomer mixture, diastereomer mixture) of the epoxy compound (1') and then optical resolution, recrystallization and the like; and the like.

The epoxytriazole derivative (2) can be derived to a triazole compound which is useful as an antifungal agent according to the methods described in JP-H04-356471A, JP-H05-230038A and the like.

PRODUCTION EXAMPLES OF THE EPOXY COMPOUND (1)

As described above, the epoxy compound (1) can be produced by converting the hydroxy group of the epoxy compound (1") into a leaving group X.

It is explained by referring to the case that the leaving group X is $OSO_2R^2$ as follows.

For example, the epoxy compound (1) wherein X is $OSO_2R^2$ can be easily produced by making the epoxy compound (1") react with the sulfonyl halide (6) or the sulfonic anhydride (7).

The reaction is usually performed in the presence of a base.

Examples of the base include aliphatic tertially amines such as trimethylamine, triethylamine, tributylamine, diisopropylethylamine and N-methylmorpholine; aromatic amines such as pyridine, picoline, 2,6-lutidine, colidine, 4-(N,N-dimethylamino)pyridine, N,N-dimethylaniline and N,N-diethylaniline; alkali metal carbonates such as sodium carbonate and potassium carbonate; and basic ion-exchange resins such as Amberlite IRA-67 and Amberlite IRA-900. Preferable are triethylamine and sodium carbonate, and more preferable is triethylamine.

The amount of the base is usually 0.8 to 3 mols, preferably 1 to 2 mols, more preferably 1 to 1.5 mols per 1 mol of the sulfonyl halide (6) or the sulfonic anhydride (7) (hereinafter, referred to as the sulfonyl halide and so on in case that these are not distinguished from each other) in view of the reaction rate, a reduction of the side reaction and economy.

Any solvent can be used so long as it does not inhibit the reaction. Examples of the solvent include methylene chloride, 1,2-dichloroethane, monochlorobenzene, 1,2-dichlorobenzene, 2-chlorotoluene, 3-chlorotoluene, 4-chlorotoluene 2-chloro-m-xylene, 2-chloro-p-xylene, 4-chloro-o-xylene, 2,3-dichlorotoluene, 2,4-dichlorotoluene, 2,5-dichlorotoluene, 2,6-dichlorotoluene, 3,4-dichlorotoluene and monofluorobenzene, nitrobenzene, carbon disulfide, toluene, acetonitrile, propionitrile, methyl tert-butyl ether, ethylene glycol dimethyl ether, diethylene glycol dimethyl ether, tetrahydrofuran, 2-methyltetrahydrofuran, 1,3-dioxolane and 1,4-dioxane. Toluene is preferable. The solvent may be a mixture containing two or more solvents, wherein any mixing ratio is available.

The amount of the solvent is usually 0.5 L to 30 L, preferably 0.8 L to 25 L, more preferably 1 L to 20 L per 1 kg of the epoxy compound (1").

The reaction temperature depends on the raw materials and their ratio used for the reaction, and it is usually −30 to +80° C., preferably −10 to +60° C., more preferably −5 to +35° C. The reaction time depends on the amount of the raw materials, and it is usually 0.5 to 10 hours, preferably 1 to 5 hours.

The order of adding of the reagents is not restricted. For example, a method of adding the epoxy compound (1") and a base to a solvent, and then adding the sulfonyl halide and so on thereto, or a method of adding the epoxy compound (1") and the sulfonyl halide and so on to a solvent, and then adding a base thereto is performed.

The present invention is explained in more detail by examples as follows; however, it is not restricted to these examples.

Yield and Chemical Purity Analysis: HPLC Conditions
  Column: Symmetry C18
    (produced by Waters Corp., 5 µm, 3.9 mm φ×150 mm)
  Mobile Phase: 20% aqueous acetonitrile solution
  Flow rate: 1.0 mL/min
  Column temperature: 35° C.
  Detective Wave Length: 210 nm
Retention time of (2R,3S)-(2,4- or 2,5-difluorophenyl)-3-methyl-2-[(1H-1,2,4-triazol-1-yl)methyl]oxirane: 15.2 minutes
Retention time of (2S,3S)-(2,4- or 2,5-difluorophenyl)-3-methyl-2-[(1H-1,2,4-triazol-1-yl)methyl]oxirane: 17.3 minutes Optical Purity Analysis (HPLC Condition-1)
  Column: Chiralcel OD-H
    (produced by Daicel Chemical Industries, 5 µm, 4.6 mm φ×250 mm)
  Mobile Phase: n-hexane/2-propanol solution (9/1; v/v)
  Flow rate: 1 mL/min
  Column temperature: 30° C.
  Detective Wave Length: 260 nm
Retention time of (2R,3S)-2-(2,4-difluorophenyl)-3-methyl-2-[(1H-1,2,4-triazol-1-yl)methyl]oxirane: 18.0 minutes
Retention time of (2S,3R)-2-(2,4-difluorophenyl)-3-methyl-2-[(1H-1,2,4-triazol-1-yl)methyl]oxirane: 24.1 minutes Optical Purity Analysis (HPLC Condition-2)
  Column: Chiralpak AD
    (produced by Daicel Chemical Industries, 10 µm, 4.6 mm φ×250 mm)
  Mobile Phase: n-hexane/ethanol/diethylamine solution (930/70/0.04; v/v)
  Flow rate: 1.2 mL/min
  Column temperature: 30° C.
  Detective Wave Length: 265 nm
Retention time of (2S,3R)-2-(2,5-difluorophenyl)-3-methyl-2-[(1H-1,2,4-triazol-1-yl)methyl]oxirane: 12.7 minutes
Retention time of (2R,3S)-2-(2,5-difluorophenyl)-3-methyl-2-[(1H-1,2,4-triazol-1-yl)methyl]oxirane: 19.6 minutes Both (2R,3R)-3-(2,4-difluorophenyl)-3,4-epoxy-2-methanesulfonyloxybutane and (2R,3R)-3-(2,5-difluorophenyl)-3,4-epoxy-2-methanesulfonyloxybutane were prepared by the method described in WO2004/000826A.

Example 1

In DMF (130 ml), (2R,3R)-3-(2,4-difluorophenyl)-3,4-epoxy-2-methanesulfonyloxybutane (82.8 g, 0.3 mol) and 1,2,4-triazole (26.7 g, 0.39 mol) were dissolved and heated to about 60° C. with stirring. 20% aqueous sodium hydroxide solution (103.8 g, 0.37 mol) was dropped thereto over about 1.5 hours and further stirred for 7 hours at the same temperature for the reaction. After the reaction, the mixture was cooled and toluene (150 ml) was added thereto. The obtained mixture was neutralized (pH 7-8) with 35% hydrochloric acid and subjected to phase separation. The water layer was extracted with toluene (150 ml) three times. The combined toluene layer was washed with diluted hydrochloric acid, aqueous sodium hydrogen carbonate solution and water subsequently, and the solvent was distilled off under a reduced pressure. The concentrated residue was subjected to recrystallization from a mixed solvent of toluene/heptane (20/80; v/v, 400 ml) to give (2R,3S)-2-(2,4-difluorophenyl)-3-methyl-2-[(1H-1,2,4-triazol-1-yl)methyl]oxirane (27.1 g, yield 36.0%, optical purity (HPLC condition-1) 100% e.e., mp 89° C.).

Example 2

The same procedure and work-up treatment as Example 1 were performed, except that 45% aqueous sodium hydroxide solution (32.9 g, 0.37 mol) was used in place of 20% aqueous potassium hydroxide solution (103.8 g, 0.37 mol), to give (2R,3S)-2-(2,4-difluorophenyl)-3-methyl-2-[(1H-1,2,4-triazol-1-yl)methyl]oxirane (27.0 g, yield 35.8%, optical purity (HPLC condition-1) 100% e.e., mp 89° C.).

Example 3

The same procedure and work-up treatment as Example 1 were performed, except that 20% aqueous potassium carbonate solution (255.7 g, 0.37 mol) was used in place of 20% aqueous potassium hydroxide solution (103.8 g, 0.37 mol), to give (2R,3S)-2-(2,4-difluorophenyl)-3-methyl-2-[(1H-1,2,4-triazol-1-yl)methyl]oxirane (26.8 g, yield 35.6%, optical purity (HPLC condition-1) 100% e.e., mp 89° C.).

Example 4

The same procedure and work-up treatment as Example 1 were performed, except that DMSO (130 ml) was used in place of DMF (130 ml), to give (2R,3S)-2-(2,4-difluorophenyl)-3-methyl-2-[(1H-1,2,4-triazol-1-yl)methyl]oxirane (27.1 g, yield 36.0%, optical purity (HPLC condition-1) 100% e.e., mp 89° C.).

Example 5

The same procedure and work-up treatment as Example 1 were performed, except that methanol (130 ml) was used in place of DMF (130 ml), to give (2R,3S)-2-(2,4-difluorophenyl)-3-methyl-2-[(1H-1,2,4-triazol-1-yl)methyl]oxirane (27.1 g, yield 36.0%, optical purity (HPLC condition-1) 100% e.e., mp 89° C.).

Example 6

The same procedure and work-up treatment as Example 1 were performed, except that iso-propanol (130 ml) was used in place of DMF (130 ml), to give (2R,3S)-2-(2,4-difluorophenyl)-3-methyl-2-[(1H-1,2,4-triazol-1-yl)methyl]oxirane (27.1 g, yield 36.0%, optical purity (HPLC condition-1) 100% e.e., mp 89° C.).

Example 7

The same procedure and work-up treatment as Example 1 were performed, except that (2R,3S)-3-(2,5-difluorophenyl)-3,4-epoxy-2-methanesulfonyloxybutane (82.8 g, 0.3 mol) was used in place of (2R,3S)-3-(2,4-difluorophenyl)-3,4-epoxy-2-methanesulfonyloxybutane (82.8 g, 0.3 mol) and that the neutralization with 35% hydrochloric acid, was carried out at pH 3-5, to give (2R,3S)-2-(2,5-difluorophenyl)-3-methyl-2-[(1H-1,2,4-triazol-1-yl)methyl]oxirane (27.1 g, yield 36.0%, optical purity (HPLC condition-2) 100% e.e., mp 69° C.).

Example 8

In DMSO (26.4 ml), (2R,3R)-3-(2,4-difluorophenyl)-3,4-epoxy-2-butanol (20.0 g, 0.1 mol) and 1,2,4-triazole (10.4 g, 0.15 mol) were dissolved and heated to about 60° C. with stirring. 20% aqueous sodium hydroxide solution (6.0 g, 0.03 mol) was dropped thereto over about 15 minutes and further stirred for 5 hours at the same temperature for the reaction. After the reaction, the mixture was cooled, diluted with water (40 ml) and neutralized (pH 6-7) with 35% hydrochloric acid. Ethyl acetate (100 ml) was added, stirred and subjected to phase separation. The water layer was extracted with ethyl acetate (100 ml) three times. A part of the ethyl acetate was taken and concentrated, and then NMR was measured to confirm the sample is (2R,3R)-2-(2,4-difluorophenyl)-1-(1H-1,2,4-triazol-1-yl)-2,3-butanediol.

$^1$H-NMR (CDCl$_3$, δ ppm) 0.98 (3H, d, J=6 Hz), 2.62 (1H, d, J=9 Hz), 4.31-4.34 (1H, m), 4.79, 4.80 (each 1H, d, J=14 Hz), 4.82 (1H, s), 6.72-6.79 (2H, m), 7.38-7.45 (1H, m), 7.83, 7.85 (each 1H, s)

The ethyl acetate layers were combined and then distilled off under a reduced pressure. Subsequently, toluene (50 ml) and triethylamine (65.8 g, 0.65 mol) were added thereto and cooled to about 5° C. and stirred. Methanesulfonyl chloride (17.2 g, 0.15 mol) was dropped thereto over about one hour and stirred for 30 minutes at the same temperature for the reaction. After the reaction, water (50 ml) was poured into and stirred, and then water layer was separated and extracted with toluene (100 ml) three times. The combined toluene layers were washed with water and the solvent was distilled off under a reduced pressure. The concentrated residue was subjected to recrystallization from a mixed solvent of toluene/heptane (20/80; v/v, 400 ml) to give (2R,3S)-2-(2,4-difluorophenyl)-3-methyl-2-[(1H-1,2,4-triazol-1-yl)methyl] oxirane. (11.6 g, yield 46.2%, optical purity (HPLC condition-1) 100% e.e., mp 89° C.)

Example 9

The same procedure and work-up treatment as Example 9 were performed, except that 20% aqueous potassium hydroxide solution (8.4 g, 0.03 mol) was used in place of 20% aqueous sodium hydroxide solution (6.0 g, 0.03 mol), to give (2R,3S)-2-(2,4-difluorophenyl)-3-methyl-2-[(1H-1,2,4-triazol-1-yl)methyl]oxirane (11.0 g, yield 43.8%, optical purity (HPLC condition-1) 100% e.e., mp 89° C.).

Example 10

The same procedure and work-up treatment as Example 9 were performed, except that DMF (26.4 ml) was used in place of DMSO (26.4 ml), to give (2R,3S)-2-(2,4-difluorophenyl)-3-methyl-2-[(1H-1,2,4-triazol-1-yl)methyl]oxirane (9.3 g, yield 37.0%, optical purity (HPLC condition-1) 100% e.e., mp 89° C.).

Example 11

The same procedure and work-up treatment as Example 1 were performed, except that (2R,3R)-3-(2,5-difluorophenyl)-3,4-epoxy-2-butanol (20.0 g, 0.1 mol) was used in place of (2R,3R)-3-(2,4-difluorophenyl)-3,4-epoxy-2-butanol (20.0 g, 0.1 mol), to give (2R,3S)-2-(2,5-difluorophenyl)-3-methyl-2-[(1H-1,2,4-triazol-1-yl)methyl]oxirane (11.3 g, yield 45.0%, optical purity (HPLC condition-2) 100% e.e., mp 69° C.).

Example 12

The same procedure as Example 8 was performed, except that the amount of triethylamine was 15.2 g (0.15 mol) in place of 65.8 g (0.65 mol) till the reaction with methanesulfonyl chloride (17.2 g, 0.15 mol). After the reaction, 20% aqueous sodium hydroxide solution (100.0 g, 0.50 mol) was dropped into the reaction solution and stirred for 30 minutes at the same temperature. (stirred and reacted in two phase separation) After the reaction, the reaction solution was allowed to stand and the phases were separated, and the water layer was extracted with toluene (100 ml) three times. The toluene layers were combined and washed with water, and the solvent was distilled off under a reduced pressure. The concentrated residue was recrystallized from a mixed solvent, namely toluene/heptane (20/80; v/v, 400 ml) to give (2R,3S)-2-(2,4-difluorophenyl)-3-methyl-2-[(1H-1,2,4-triazol-1-yl) methyl]oxirane (11.4 g, yield 45.4%, optical purity (HPLC condition-1) 100% e.e., mp 89° C.).

According to the present invention, the epoxytriazole derivative (2) which is useful as a synthetic intermediate for an antifungal agent can be produced effectively in a simple procedure.

What is claimed is:

1. A process for producing an epoxytriazole derivative represented by formula (2):

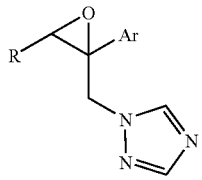 (2)

(wherein R and Ar are defined below),
which comprises a step including a reaction of an epoxy derivative represented by formula (1'):

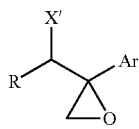 (1')

(wherein R represents a hydrogen atom or C1-12 alkyl group and Ar represents an aromatic group optionally substituted by a halogen atom(s) or trifluoromethyl group(s), and X' represents a hydroxy group or leaving group), with 1,2,4-triazole in the presence of a base and water.

2. The process described in claim 1, wherein the epoxy derivative (1') is an epoxy compound represented by formula (1):

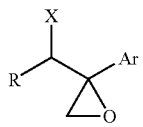 (1)

(wherein X represents a leaving group, and R and Ar are defined above).

3. The process described in claim 2, wherein the leaving group is —SO$_2$R$^2$ (wherein R$^2$ represents an optionally substituted C1-12 alkyl group or optionally substituted aromatic group).

4. The process described in claim 3, wherein R$^2$ is a methyl group.

5. The process described in claim 2, wherein Ar is a difluorophenyl group.

6. The process described in claim 5, wherein the difluorophenyl group is a 2,4-difluorophenyl group or 2,5-difluorophenyl group.

7. The process described in claim 2, wherein R is a methyl group.

8. The process described in claim 2, wherein the base is at least one selected from the group consisting of alkali metal hydroxide, alkaline earth metal hydroxide, alkali metal carbonate and alkaline earth metal carbonate.

9. The process described in claim 8, wherein the alkali metal is sodium or potassium and alkaline earth metal is calcium or magnesium in at least one selected from the group consisting of alkali metal hydroxide, alkaline earth metal hydroxide, alkali metal carbonate and alkaline earth metal carbonate.

10. The process described in claim 3, wherein the epoxy derivative represented by formula (1), wherein X is a —SO$_2$R$^2$ (wherein R$^2$ is defined above), is obtained by the reaction of the epoxy compound represented by formula (1"):

 (1")

(wherein R and Ar are defined above),
with a sulfonyl halide represented by formula (6):

(wherein Y' represents a chlorine atom or bromine atom and R$^2$ is defined above), or a sulfonic anhydride represented by formula (7):

(wherein R$^2$ is defined above).

11. The process described in claim 1, wherein the epoxy derivative represented by formula (1') is the epoxy compound represented by formula (1"), the step provides a dihydroxy compound represented by formula (3):

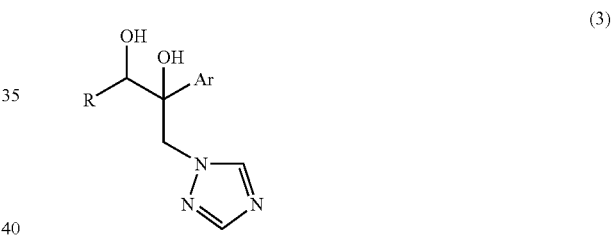 (3)

(wherein R and Ar are defined above),
and further comprising a step of a reaction of the dihydroxy compound (3) with a compound represented by formula (5):

 (5)

(wherein R$^1$ represents an optionally substituted C1-12 alkyl group or optionally substituted aromatic group and Y represents a chlorine atom or bromine atom), in the presence of a base.

12. The process described in claim 11, wherein the epoxytriazole derivative represented by formula (2) is an optically active isomer.

13. The process described in claim 11, wherein Ar is a difluorophenyl group.

14. The process described in claim 13, wherein the difluorophenyl group is a 2,4-difluorophenyl group or 2,5-difluorophenyl group.

15. The process described in claim 11, wherein R is a methyl group.

16. The process described in claim 11, wherein the base for the reaction step of the epoxy compound represented by formula (1") with 1,2,4-triazole is at least one selected from the group consisting of alkali metal hydroxide, alkaline earth metal hydroxide, alkali metal carbonate and alkaline earth metal carbonate.

17. The process described in claim 16, wherein the alkali metal is sodium or potassium and the alkaline earth metal is calcium or magnesium in alkali metal hydroxide, alkaline earth metal hydroxide, alkali metal carbonate and alkaline earth metal carbonate.

18. The process described in claim 11, wherein the base for the reaction step of the dihydroxy compound represented by formula (3) with the compound represented by formula (5) is at least one selected from the group consisting of organic amine, alkali metal hydroxide and alkali metal carbonate.

19. The process described in claim 18, wherein the organic amine is triethylamine or pyridine and the alkali metal is sodium or potassium.

20. A process for producing a dihydroxy compound of the formula (3):

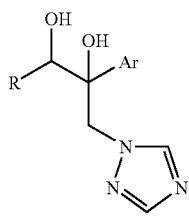
(3)

(wherein R and Ar are defined below),
which comprises making an epoxy compound represented by formula (1"):

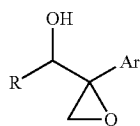
(1")

(wherein R represents a hydrogen atom or C1-12 alkyl group and Ar represents an aromatic group, and at least one hydrogen atom of said aromatic group may be substituted by a halogen atom(s) or trifluoromethyl group(s)), react with 1,2,4-triazole in the presence of a base and water.

21. The process described in claim 20, wherein Ar is a difluorophenyl group.

22. The process described in claim 21, wherein the difluorophenyl group is a 2,4-difluorophenyl group or 2,5-difluorophenyl group.

23. The process described in claim 20, wherein R is a methyl group.

24. The process described in claim 20, wherein the base is at least one selected from the group consisting of alkali metal hydroxide, alkaline earth metal hydroxide, alkali metal carbonate and alkaline earth metal carbonate.

25. The process described in claim 24, wherein the alkali metal is sodium or potassium and alkaline earth metal is calcium or magnesium in alkali metal hydroxide, alkaline earth metal hydroxide, alkali metal carbonate and alkaline earth metal carbonate.

* * * * *

UNITED STATES PATENT AND TRADEMARK OFFICE
CERTIFICATE OF CORRECTION

PATENT NO. : 7,569,699 B2  Page 1 of 1
APPLICATION NO. : 11/791511
DATED : August 4, 2009
INVENTOR(S) : Taro Ishibashi, Hideo Muraoka and Tadashi Mizuno It is certified that error appears in the above-identified patent and that said Letters Patent is hereby corrected as shown below:

On the Title Page, Item (75) should read:

-- (75)   Inventors:   Taro Ishibashi, Nagaokakyo (JP); Hideo Muraoka, Toyonaka (JP); Tadashi Mizuno, Ibaraki (JP) --

Signed and Sealed this

Fifteenth Day of September, 2009

David J. Kappos
*Director of the United States Patent and Trademark Office*